United States Patent [19]
Watanabe et al.

[11] Patent Number: 5,690,981
[45] Date of Patent: Nov. 25, 1997

[54] LOW CALORIE FOODSTUFF, AQUEOUS PASTE COMPOSITION, AS WELL AS PRODUCTION PROCESS THEREOF

[75] Inventors: Kunihiko Watanabe; Hideo Kanoh; Shigeru Yamanaka; Atsushi Okiyama; Takahide Kawanishi, all of Kawasaki, Japan

[73] Assignee: Ajinomoto Co., Inc., Tokyo, Japan

[21] Appl. No.: 518,016

[22] Filed: Aug. 22, 1995

Related U.S. Application Data

[63] Continuation of Ser. No. 369,261, Jan. 5, 1995, abandoned, which is a continuation of Ser. No. 247,409, May 23, 1994, abandoned, which is a continuation of Ser. No. 1,223, Jan. 6, 1993, abandoned, which is a continuation of Ser. No. 723,651, Jun. 26, 1991, abandoned, which is a continuation of Ser. No. 565,576, Aug. 10, 1990, abandoned, which is a continuation-in-part of Ser. No. 395,573, Aug. 18, 1989, abandoned.

[30] Foreign Application Priority Data

| Aug. 23, 1988 | [JP] | Japan | 63-208562 |
| Oct. 7, 1988 | [JP] | Japan | 63-253490 |
| Feb. 21, 1989 | [JP] | Japan | 1-40672 |
| Apr. 17, 1989 | [JP] | Japan | 1-96780 |

[51] Int. Cl.$^6$ ............................................. A23L 1/05
[52] U.S. Cl. .................. 426/531; 426/573; 426/804; 426/574
[58] Field of Search ............................ 426/531, 573, 426/804, 574

[56] References Cited

U.S. PATENT DOCUMENTS

| 3,023,104 | 2/1962 | Battista | 426/804 |
| 3,973,051 | 8/1976 | Buckley et al. | 426/574 |
| 3,982,003 | 9/1976 | Mitchell et al. | 426/1 |
| 4,089,981 | 5/1978 | Richardson | 426/104 |
| 4,414,229 | 11/1983 | Bakal et al. | 426/603 |
| 4,451,489 | 5/1984 | Beale et al. | 426/254 |
| 4,668,519 | 5/1987 | Dartey et al. | 426/548 |
| 4,676,976 | 6/1987 | Toba et al. | 426/573 |
| 4,684,533 | 8/1987 | Kratochvil | 426/576 |
| 4,741,907 | 5/1988 | Furuhashi | 426/94 |
| 4,774,095 | 9/1988 | Kleinschmidt et al. | 426/579 |
| 4,844,913 | 7/1989 | Ogawa | 426/18 |
| 4,900,571 | 2/1990 | Kammuri et al. | 426/656 |
| 4,911,946 | 3/1990 | Singer et al. | 426/567 |

FOREIGN PATENT DOCUMENTS 58-190369  11/1983  Japan.

OTHER PUBLICATIONS

Patent Abstracts of Japan C132. vol. 6, No. 219 (for Japan Kokai 57–122748) published Nov. 2, 1982.

Brodribb et al. "Effect of Bran Particle Size on Stool Weight." GUT. 1978. vol. 19. pp. 60–63.

*Primary Examiner*—Anthony J. Weier
*Attorney, Agent, or Firm*—Oblon, Spivak, McClelland, Maier & Neustadt, P.C.

[57] ABSTRACT

The invention relates to (a) a low calorie foodstuff containing, as a substitute for protein, carbohydrate and/or oil and fat, from 0.7 to 10% by weight, based on the dry weight, of dietary fibers with a size of not greater than 80 μm and a retained water amount of 9 or greater, (b) an aqueous paste-like composition of from 5 to 40% by weight of from spherical to fibrous dietary fibers of not greater than 5 μm of diameter or length, and (c) an aqueous paste-like composition, which contains from 5 to 40% by weight of dietary fibers, the dietary fibers being in the form of gel particles having a particle size of not greater than 80 μm, as well as the production method.

7 Claims, No Drawings

LOW CALORIE FOODSTUFF, AQUEOUS PASTE COMPOSITION, AS WELL AS PRODUCTION PROCESS THEREOF

This application is a Continuation of application Ser. No. 08/369,261, filed on Jan. 5, 1995, abandoned; which is a Continuation of Ser. No. 08/247,409, filed on May 23, 1994, abandoned; which is a Continuation of Ser. No. 08/001,223, filed on Jan. 6, 1993, abandoned; which is a Continuation of Ser. No. 07/723,651 filed on Jun. 26, 1991, abandoned; which is a Continuation of Ser. No. 07/565,576 filed on Aug. 10, 1990, abandoned; which is a Continuation-in-Part of Ser. No. 07/395,573 filed on Aug. 18, 1989, abandoned.

BACKGROUND OF THE INVENTION

The present invention concerns foodstuff capable of reducing calorie without worsening the texture.

For the foodstuff of this type, it has been known to blend powder of crystallite aggregates of cellulose mainly consisting of particles over a standard 200 mesh sieve (greater than 74 µm) as a substitute for starch materials (Japanese Patent Publication (Kokoku) No. Sho 43-15,762). In this low calorie foodstuff, since the addition amount of fine cellulose powder is as much as 10 to 50% of the entire composition, it gives rough feeling to worsen the texture. In addition, since the addition is limited only to starch materials, it can not be blended with other materials and, therefore, can not cope with the demand at present of reducing calorie of various foodstuffs ranging from cake, bread, etc. to processed meat such as ham and sausage.

In view of the foregoing demand, it is a first object of the present invention to provide low calorie foodstuffs which are not restricted to specific kinds of foodstuffs such as noodles, cake, bread, etc. mainly composed of carbohydrate or ham and sausage mainly composed of protein, and which do not worsen the texture inherent to foodstuffs, i.e., touch to the tongue or flavor.

The present invention also concerns an aqueous paste-like composition containing dietary fibers, which can be used generally as raw material, for example to foodstuffs, cosmetics, industrial materials, etc.

In the field of foodstuffs, dietary fibers have now been considered as a so-called sixth nutrient in addition to carbohydrate, protein, lipid, vitamins and minerals and begun to attract attention. It has been said that dietary fibers have effects of improving the intestinal flora of microorganisms, adsorption of pernicious substances, promotion of peristaltic movement of intestines, etc. Fibrous or finely particulate forms of dietary fibers have been known including, for example, from short fibers of 0.015 to 0.02 nm width and 0.5 µm length to particulate fibers of a diameter of about several µm, for example, in a case of cellulose.

On the other hand, paste-like oils and fats typically represented by margarine, such as butter, margarine, cheese, whipping cream and mayonnase are being used as raw materials for various foodstuffs and in cooking by utilizing their particular texture. However, it is considered in the field of foodstuffs that paste-like oils and fats typically represented by margarine, etc. are of high calorie and lead to obesity, hypertension, heart disease, etc.

In the field of cosmetics, paste-like products having creamy appearance are being used generally, and a lot of oils and fats are incorporated in them. However, creams containing oils and fats are not pleasant since they give sticky touch upon applying on skins.

Under the foregoing situations, a second object of the present invention is to provide an aqueous paste-like composition which can overcome the foregoing drawbacks, and which is of low calorie, organoleptically acceptable, as well as not sticky and, thus, comfortable skin touch.

SUMMARY OF THE INVENTION

For attaining the first object, the low calorie foodstuff according to the present invention comprises, as a substitute for protein, carbohydrate and/or oil and fat, from 0.7 to 10% by weight, on the dry basis, of dietary fibers with an average grain size of not greater than 80 µm and a retained water amount of not less than 9.

For attaining the foregoing second object, the present inventors have made earnest studies and, as a result, have accomplished the present invention based on the findings that a paste-like material obtained by properly using one or more of methods such as pulverization, partial decomposition, dissolution, and re-precipitation after dissolution can reduce the calorie of food remarkably or almost to zero, when it is blended with foodstuffs without worsening their inherent texture, as well as can eliminate sticky feeling of cosmetic creams applied on skins when the paste-like material is blended with such cosmetic creams.

That is, the present invention provides also such aqueous paste-like composition as described above and a production process thereof.

DETAILED DESCRIPTION OF THE INVENTION

First Embodiment

At first, low calorie foodstuffs concerning the first object to be solved by the present invention are to be described specifically.

According to the present invention, dietary fibers mean those food ingredients not digested by human digesting enzymes. As typical examples thereof, there can be mentioned natural dietary fibers such as burdock fibers, wheat bran, konjak mannan, and apple fibers, and disintegration products of bacterial celluloses such as those yielded by culturing bacteria such as Acetobacter aceti subsp. xylinum ATCC 10821, ATCC 10245, etc.

Generally, dietary fibers are from spherical to rod-like shape and their water holding capability is reduced as their size is smaller. They can be a highly water retaining material capable of reducing the calorie of foodstuffs without deteriorating the texture if they are restricted in size to a specific range. The present invention has been accomplished based on such findings.

The size of the dietary fibers blended with foodstuffs (grain size for spherical dietary fibers and length for rod-like dietary fibers) is about not greater than 80 µm and, preferably, not greater than 30 µm. Konjak mannan having a size of at least 5 µm is preferably used. If the size exceeds about 80 µm, they give rough and unpleasant touch, thereby deteriorating the texture. It is very easy for those skilled in the art to produce dietary fibers within such a size range. Refer to examples described later.

Further, the retained water amount of dietary fibers is determined herein, as follows; Dietary fibers in a water content equilibrium are centrifugalized at 14,000 g; The supernatant is removed to give a remaining precipitated residue; And, from the remaining precipitated residue is calculated the retained water amount per unit weight of the dietary fibers. See "Dietary Fibers", edited by S. Innan and S. Kiriyama, published by Daiichi Shuppan Co., p. 57 (1982). The reason why the retained water amount is restricted to about not less than 9 is that the fibers can not sufficiently occlude water and fail to give physical properties similar to those of protein, carbohydrate and oils and fats if the amount is smaller than 9. The dietary fibers are blended in an amount of 0.7 to 10% by weight, preferably 1.0 to 2.0% by weight on the dry basis, based on the total weight of the foodstuff. Reduction of calorie is insufficient if the retained water amount is not greater than 0.7% by weight, whereas if it exceeds 10% by weight, the texture of cellulose becomes conspicuous, making foodstuffs coarser and less swallowable.

There is no particular restrictions on the method of blending the dietary fibers and there can be employed any of desired means, for example, a method of mixing soft wheat flour and powdery dietary fibers and then kneading them with water, or kneading paste-like dietary fibers with ground fish and meat.

The dietary fibers are almost tasteless and odorless and thus give no substantial effects on the flavor of various seasonings, for example, soy sauce, sauce, miso or tasty seasonings, or various spices such as onion, garlic, turmeric or curry.

The low calorie foodstuffs according to the present invention comprise, as a substitute for part or all of protein, carbohydrate and/or oil and fat, dietary fibers which are tasteless and odorless, have high retained water amount and are compatible with protein, carbohydrate or oil and fat. For instance, the low calorie foodstuffs such as ham and sausage have flavor or texture quite similar to those of usual foodstuffs such as ham or sausage not blended with dietry fibers. In addition, since there is no particular restrictions on the method of blending the dietary fibers and, therefore, they can be incorporated as they are into the conventional production step, the production is also easy.

The present invention is to be explained specifically referring to the following examples.

EXAMPLE 1

400 ml of an aqueous culture medium comprising 5 g/dl of sucrose, 0.5 g/dl of amino acid mixture, 0.1 g/dl of phytic acid, 0.3 g/dl of monopotassium phosphate, 0.1 g/dl of magnesium sulfate 7 hydrate and 0.1 g/dl of ammonium sulfate and having a pH value of 5 was charged into a 500-ml Sakaguchi flask and sterilized by heating at 120° C. for 20 min.

Then, Acetobacter aceti subsp. xylnum ATCC 10821 precultured in a culture medium of the same composition at 30° C. for three days was inoculated and cultured under shaking at 30° C. for 2 days. The resulting culture both was adjusted to pH 4 and then static cultured at 30° C. for 15 days. The gel-like cellulose material of 13–15 mm thickness formed in the upper layer was collected. It was cut into pieces of a size of about 3 cm×3 cm and washed in a running water for 24 hours.

Further, the cut cellulose was immersed in an aqueous 0.5N solution of sodium hydroxide for 3 days, then neutralized with 0.5N hydrochloric acid and washed with running water for one day.

The thus washed cellulose was dispersed in the same amount by weight of water, subjected to disintegration for 25 min using a pulp disintegrator (manufactured by Kumagaya Seisakusho Co.) and then subjected 10 times to the homogenizing treatment at 100 kg/cm$^2$ by using a high pressure homogenizer (manufactured by Manton Gaulin Co.).

The liquid suspension prepared as described above was centrifugalized at 14,000 g for 10 min to remove the supernatant, whereby an Acetobacter-produced cellulose disintegration product (hereinafter, simply referred to as cellulose disintegration product) was obtained.

The solid content of the cellulose disintegration product, when measured, was 8.0% and the retained water amount was 11.5 (g-water/g-dry dietary fibers). Further, the size of the dietary fibers contained in the cellulose disintegration product was not greater than 80 μm, and the average grain size, when measured by a Microtrac particle-size analyzer (manufactued by Nikkisei Co.), was 20 μm. Low calorie hamburger was prepared by substituting the cellulose disintegration product for 30% of beef.

The formulation is as shown in Table 1.

TABLE 1

|  | Control | Low calorie hamburger |
|---|---|---|
| Egg | 70 g | 70 g |
| Bread crumbs | 40 | 40 |
| Beef | 400 | 280 |
| Cellulose disintegration product | 0 | 120 |
| Salt | 3.5 | 3.5 |
| Pepper | 0.6 | 0.6 |
| Onion | 80 | 80 |
| Butter | 12.5 | 12.5 |
| Beef extract | 0 | 4 |

The calorie of the control product was 1,600 kcal, while the calorie of the low calorie hamburger according to the present invention was 1,240 kcal and, thus, 23% calorie reduction was attained.

The content of the dietary fibers in the low calorie hamburger was 1.6% and the texture was quite similar as compared with that of the control.

EXAMPLE 2

Sausage of 30% calorie reduction was prepared with the formulation as shown in Table 2 below by using the same cellulose disintegration product as in Example 1 as a substitute for oils and fats (lard).

At first, a blend of soy protein, water and lard (for the control) was subjected to a Stephen cutter treatment to previously prepare emulsion curds. Then, pork and various seasonings were roughly cut in a Stephen cutter at 1,500 rpm, to which the emulsion curds as described above was added to prepare mixed meat.

The mixed meat was charged in a casing tube and, after drying at 60° C. for 10 min, was subjected to a smoking treatment at 65° C. for 10 min followed by boiling at 75° C. for 30 min and cooling, whereby Vienna sausage was prepared. The same blend of soy protein, water and lard but with the lard having been partially substituted with the cellulose disintegration product (for the low calorie sausage) was processed in the same way, whereby another Vienna sausage was prepared.

The calorie of the control was 7,500 kcal, while the calorie of the low calorie Vienna sausage was 5,250 kcal in which 30% calorie reduction was attained.

The content of the dietary fibers in the low calorie Vienna sausage was 0.8% and the texture was quite similar as compared with the control.

TABLE 2

| Emulsion curds | Control | Low calorie Vienna sausage |
|---|---|---|
| Soy bean protein | 125 g | 125 g |
| Water | 500 | 500 |
| Lard | 375 | 125 |
| Cellulose disintegration product | — | 250 |
| | 1000 | 1000 |
| Formulation: | | |
| Emulsion curds | | 1000 g |
| Pork meat | | 1000 |
| Salt | | 42.6 |
| Wheat starch | | 65.0 |
| Sugar | | 30.0 |
| Inocinic acid | | 10.0 |
| Water | | 350 |
| W pepper | | 7.6 |
| Sage | | 2.6 |
| All spice | | 2.6 |
| NaNO$_2$ | | 0.6 |
| Na L-ascorbate | | 1.6 |
| Na Polyphosphate | | 7.6 |
| | | 2520.2 |

EXAMPLE 3

Bean jam of 30% calorie reduction was prepared by the formulation as shown in Table 3 by using the same cellulose disintegration product as in Example 1 as a substitute for sugar.

The bean jam was produced in accordance with the customary method except for preparing an emulsion of the cellulose disintegration product previously put together with water to a homogenizer.

TABLE 3

| Raw material | Control | Low calorie bean jam |
|---|---|---|
| Raw strained bean jam | 200 g | 200 g |
| (red bean, kidney bean) | 200 | 200 |
| High grade sugar | 140 | 67 (including 6 g powder sugar) |
| Starch syrup | 25 | 33 |
| Salt | 0.3 | 0.3 |
| Cellulose disintegration product | — | 40 |
| Aspartame | — | 0.5 |
| Water | 130 | 173 |
| Total | 495.3 | 513.8 |
| Finished amount | 400 g | 410 g |
| Finished water content | 41% | 58% |
| Calorie | 232 kcal/100 g | 163 kcal/100 g |

As apparent from Table 3, the low calorie bean jam showed 30% calorie reduction as compared with the control and there was no difference in sweetness and texture as compared with the control.

The content of the dietary fibers in the low calorie bean jam was 0.8%.

EXAMPLE 4

Porridge of rice and vegetables of 75% calorie reduction was prepared as shown below by using the same cellulose disintegration product as in Example 1 as a substitute for the dried rice as one of the raw materials of the porridge of rice and vegetables (manufactured by Ajinomoto Co.).

350 ml of hot water was added to 35 g of dried rice (control), and, to the mixture, seasoning soup (containing lactose, seasoning, starch, table salt, meat extract, sugar, spice, sesami oil, and chiken meat) and solid ingredients (minced shrimp, aspidium, cabbage, shiitake (mushroom), Welsh onion) were added under boiling. Then, the mass was cooked over a low flame for 5 min.

The same procedure was repeated except that the same cellulose disintegration product as in Example 1 was used instead of the dried rice, whereby a low calorie porridge was obtained.

The calorie of the control was 190 kcal, while the calorie of the low calorie porridge of rice and vegetables was 50 kcal in which 75% calorie reduction was attained.

EXAMPLE 5

Rolled omelet of 20% calorie reduction was prepared in accordance with the formulation as shown in Table 4 by using burdock dietary fibers which had been finely pulverized under liquid nitrogen freezing into fine powder of not more than 74 µm grain size, the retained water amount being 10 (g-water/g-dry dietary fibers).

The rolled omelet was prepared by baking the material cast into an egg baking plate in an oven till it was coagulated, turning the cast and baked layer upside down while hot on a shaping sheet, rolling the layer and then slicing the roll diametrically, followed by arranging on a dish.

A control rolled omelet was prepared by the same procedure except that no burdock dietary fibers or water were used.

TABLE 4

| | Control | Low calorie rolled omelet |
|---|---|---|
| Cake of pounded fish (hanpen) | 300 g | 0 g |
| Burdock dietary fiber | 0 | 100 |
| Water | 0 | 200 |
| Eggs | 9 | 9 |
| Soft wheat flour | 4 tablespoons | 4 tablespoons |
| Table salt | 1 teaspoon | 1 teaspoon |
| Sugar | 5 tablespoons | 5 tablespoons |
| Sweet sake (mirin) | 3 tablespoons | 3 tablespoons |
| Soy source | 1 teaspoon | 1 teaspoon |
| Salad oil | 1 teaspoon | 1 teaspoon |
| Calorie | 1,550 kcal | 1,250 kcal |

EXAMPLE 5a (a) 2 g of xanthan gum and 2 g of glucomannan previously dissolved in 500 g of water, 50 g of skim milk and 0.1 g of AP (Aspartame) dissolved in 366 g of water, and 20 g of burdock fibers (10 to 80 µm grain size) were mixed under stirring at 8000 rpm for 2 min in a ultra-homogenizer manufactured by Nihon Seiki Seisakusho Co. To the mixture, 10 g of butter oil and 50 g of palm seed oil previously melted by heating were added and stirred moderately at 2000 rpm for 2 min. Then, the resulting mixture was cast into a die and solidified in a refrigerator.

In this way, a bavarois- or mousse-like dessert was obtained.

The composition of the materials of the thus obtained dessert was as shown in Table 4A.

TABLE 4A

| | |
|---|---|
| Palm seed oil | 50 g |
| Butter oil | 10 |
| Xanthan gum | 2 |
| Glucomannan | 2 |
| Skim milk | 50 |
| Burdock fiber | 20 |
| Water | 865 |
| AP | 1 |
| | 1000 g |

The calorie of the dessert was reduced by 44% as compared with a comparative dessert obtained by using, instead of AP, 200 g of sugar showing the same extent of sweetness.

(b) For the comparison, a dessert was prepared quite in the same procedures as described in (a) above except for replacing 20 g of the burdock fibers with 20 g of water in the composition shown in Table 4A.

The composition of the raw materials in this case was as shown in Table 4B.

TABLE 4B

| | |
|---|---|
| Palm seed oil | 50 g |
| Butter oil | 10 |
| Xanthan gum | 2 |
| Glucomannan | 2 |
| Skim milk | 50 |
| Water | 886 |
| AP | 0.1 |
| | 1000 g |

After mixing and stirring the materials, they were cast into a die and cooled in a refrigerator.

The thus obtained dessert showed poor shape-retainability and caused water separation. That is, in the attempt of calorie reduction by using AP, a prepared dessert shows poor shape retainability and water release if burdock fibers are not used.

EXAMPLE 5b (a) 75 g of table salt, 37 g of burdock fibers (10 to 80 μm grain size), 500 g of vinegar, 750 g of yolk (9.40% of lecithin content), 1.2 g of AP and 2386.8 g of water were preliminarily mixed in a vacuum emulsifying device manufactured by Mizuho Kogyo Co., and then the mixture was emulsified under stirring moderately at about 2000 rpm while adding 1250 g of corn oil at a rate of 125 g/min. Thereafter they were mixed under stirring at a high speed for 5 min under a reduced pressure of 60–65 mmHg to obtain a mayonnaise-like emulsion.

The composition of the raw materials of the thus prepared emulsion was as shown in Table 4C.

TABLE 4C

| | |
|---|---|
| Yolk | 750 g |
| Vinegar | 500 |
| Corn oil | 1250 |
| Burdock fiber | 37 |
| AP | 1.2 |
| Water | 2386.8 |

TABLE 4C-continued

| | |
|---|---|
| Table salt | 75 |
| | 5000 g |

The mayonnaise-like emulsion had similar feeling upon eating to that of usual mayonnaise and remained in a stable emulsified state for three months when stored in a refrigerator (at 4° C.).

The mayonnaise-like emulsion had 286.3 Kcal of calorie and showed about 60% calorie reduction as compared with usual mayonnaise since the oil and fat content could be reduced by 64% and aspartame was used instead of sugar.

(b) For the comparison, a mayonnaise-like emulsion was obtained quite in the same procedures as those in (a) above except for replacing 37 g of burdock fibers with 37 g of water in the composition of the materials shown in Table 4C.

The raw material composition was as shown in Table 4D.

TABLE 4D

| | |
|---|---|
| Yolk | 750 g |
| Vinegar | 500 |
| Corn oil | 1200 |
| AP | 1.2 |
| Water | 2423.8 |
| Table salt | 75 |
| | 5000 g |

The calorie-reduced mayonnaise-like emulsion thus prepared showed low viscosity and caused segregation after 2 hours. That is, in an attempt of calorie reduction while reducing the oil and fat content and using AP (aspartame), the emulsion stability is poor if burdock fibers are not used.

EXAMPLE 5A (a) 250 g of gelatin previously swollen by 500 g of water was warmed to 50° C. to be dissolved. 450 g of skim milk, 7.5 g of aspartame, 300 g of apple fibers, said apple fibers having been prepared by finely pulverizing coarse apple fibers under liquid nitrogen freezing into fine powder of 10 to 80 μm grain size, and having a retained water amount of 10 (g-water/g-dry dietary fibers), and 6245.2 g of water were added to the solution and mixed at 5000 rpm for 3 min in a ultra-homomixer Model UM-3 manufactured by Nihon Seiki Seisakusho Co. Then, 500 g of palm seed oil and 250 g of butter oil previously melted by heating at 50° C. were added and they were further stirred at 7000 rpm for 5 min by the homomixer as described above. Finally, after foaming 2000 g of egg white by a whipper, it was added to the homomixer containing the emulsified mixture prepared as above, moderately stirred at 1500 rpm so as not to crush the foams of egg white, distributed into respective dies, and cooled and solidified in a refrigerator (4° C.) to obtain mousse-like low calorie desserts.

The composition of the raw materials of the low calorie dessert was as shown in Table 4E.

TABLE 4E

| | |
|---|---|
| Palm seed oil | 500 g |
| Butter oil | 250 |
| Skim milk | 450 |
| Gelatin | 250 |

TABLE 4E-continued

| | |
|---|---|
| Apple fiber | 300 |
| Egg white | 2000 |
| Aspartame | 7.5 |
| Water | 6242.5 |
| | 10000 g |

The low calorie dessert had a similar feeling upon use to that of usual mousse, did not release water and showed satisfactory appearance after the elapse of one day.

The low calorie dessert had 104.8K cal of calorie which corresponded to about 58% of calorie reduction as compared with usual mousse.

(b) For the comparison, a mousse-like dessert was prepared quite in the same procedures as those in (a) above except for replacing 300 g of the apple fibers with 300 g of water in the composition shown in Table 4E.

The composition of the raw material was as shown in Table 4F.

TABLE 4F

| | |
|---|---|
| Palm seed oil | 500 g |
| Butter oil | 250 |
| Skim milk | 450 |
| Gelatin | 250 |
| Egg white | 2000 |
| Aspartame | 7.5 |
| Water | 6542.5 |
| | 10000 g |

The thus prepared mousse-like dessert released water after storing in a refrigerator overnight and had low commercial value accordingly. In an attempt of calorie reduction by using aspartame, water release is caused if apple fibers are not used.

As apparent from the foregoing examples, according to the present invention, it is possible to provide low calorie foodstuffs possessing quite similar flavor or texture inherent to original foodstuffs over a wide range of foodstuffs.

Second Embodiment

Then, description is to be made for the aqueous paste-like composition, as well as production process thereof as the second object of the present invention. The present inventors, as a result of a further study of the dietary fibers, has succeeded in developing a further wide application use for dietary fibers or hydrogel thereof both having an appropriate size.

The dietary fibers according to the present invention mean those high molecular substances that are hardly digested in the human body. Specifically, they include soybean meal, soybean curd refuse (okara), used tea leaves, endodermis and peelings of citrus fruits, bran of cereals, such as wheat bran, barley bran, rye bran, and oat bran, soybean husk, apple fibers, konjak mannan, agar, pectin, alginic acid and carrageenan. Accordingly, the dietary fibers in the present invention include also those food ingredients that are not decomposed with human digestive enzymes, for example, natural dietary fibers such as burdock fibers, etc. and disintegration products of bacterial celluloses yielded by culturing bacteria such as Acetobacter aceti subsp. xylinum, ATCC 10821, ATCC 10245, etc.

Among the dietary fibers as described above, konjak mannan, agar, pectin, alginic acid, carrageenan, etc. are used in the state of hydrogel according to the present invention.

The dietry fibers of the shape and the size as described above can be obtained by properly using one or more of methods such as pulverization, partial decomposition, dissolution, re-precipitation after dissolution, etc.

Pulverization can be conducted either by dry or wet process by using a commercially available mill.

Partial decomposition may be conducted by using acid decomposition, alkali decomposition, enzymatic decomposition etc. either alone or in combination of two or more thereof.

Solvent used for the dissolution may be aqueous or organic and the dissolution may be conducted at an appropriate pH, temperature and concentration. Re-precipitation after the dissolution with such solvent can be carried out by varying the temperature and/or pH, concentration, addition of other solvent, addition of appropriate ions, etc. or a combination thereof.

For instance, an aqueous paste-like composition according to the present invention is obtained by using soybean husk as described below.

At first, soybean husk is coarsely pulverized such that it can pass through a sieve of about 40 mesh/inch. Coarse pulverization may be conducted for about 30 sec. by using a commercially available motor-driven portable coffee mill, mortar, etc. in a small-scale preparation, or by using an industrial crusher in a case of mass production. After boiling the coarse pulverization product in an aqueous 0.1–3% solution of NaOH, KOH, or the like at 70°–100° C. for about 10 min–2 hours and removing those ingredients such as protein and fats, it is caused to swell in an aqueous 8–20% solution of NaOH or KOH for 10 min to 2 hours. Then, it is hydrolyzed using 0.5–6N hydrochloric acid, sulfuric acid, nitric acid, phosphoric acid, etc. at a temperature not lower than 80° C. for 0.5 to 3 hours.

After neutralization, the residue can be recovered by centrifugation (1,000 g or greater for 10 min or longer) or filtration using customary filter paper, to obtain paste-like products. The solid content, i.e., dry matter, in the paste-like product can be from about 5–40% by weight and the resultant product becomes harder as the solid content is larger, vice versa, and the solid content may be selected depending on the application use.

With respect to the aqueous paste according to the present invention, the aqueous medium may consist only of water. Depending on the purposes, other ingredients may be incorporated, for example, a water-soluble organic solvent such as ethanol or glycerine, or surface active agent. In a case where the paste is used for other application use than the foodstuffs or cosmetics, for example, detergent, it is possible to properly blend organic or inorganic acids, as well as sterilizing ingredient, for example, cresol in addition to the surface active agent. Further, perfume, pigment and colorant may also be added property depending on the application use.

In the aqueous paste-like composition as described above, the dietary fibers are contained directly in an appropriate shape and size. On the other hand, if the dietary fibers are incorporated in the state of hydrogel, an aqueous paste-like composition having similar property may also be formed as detailed below.

In greater detail, there can be mentioned an aqueous paste-like composition containing from 5 to 40% by weight of dietary fibers as hydrogel with a particle size of not greater than 80 μm, that is, the aqueous paste-like composition contains the dietary fibers in the state of hydrogel with a particle size of not greater than 80 μm, in which the solid content of the dietary fibers is from 5 to 40% by weight based on the entire composition. If the particle size of the hydrogel is over 80 μm, the composition lacks in smoothness. Konjak mannan hydrogel having a size of at least 5 μm is preferably used (Examples 28 and 29). The solid content of the dietary fibers based on the entire composition is determined in view of the fluidity.

In the aqueous paste-like composition, there may be blended a thickening agent; oil and fat, optionally with a thickening agent; water, optionally with a thickening agent and/or an emulsifier; oil and fat and water, optionally with an emulsifier and/or a thickening agent.

As preferred hydrogel of the dietary fibers can be mentioned konjakgel, agar gel, pectin-Ca or -Mg gel, alginic acid-Ca or -Mg gel, carrageenan-Ca or -Mg gel, and a mixture of two or more thereof. The konjak gel is so-called "konjak", which is prepared by dissolving konjak mannan into water and gelatinizing with an alkali. The agar gel is so-called "agar", which is prepared from transparent gelatine film or powder obtained by freeze-drying the viscous liquid of Gelidium amansii. Pectin-Ca or -Mg gel, alginic acid-Ca or -Mg gel and carrageenan-Ca or -Mg gel are, respectively, prepared by dissolving pectin, alginic acid and carrageenan into water and then cross-linking with Ca or Mg ions.

The particle size of the hydrogel of such dietary fibers in the aqueous paste-like composition is not greater than 80 μm and, preferably, not greater than 50 μm, as described above.

The aqueous paste-like composition containing the dietary fibers in the state of hydrogel and, further, blended with a viscosity improver, oil and fat, emulsifier, water, etc., as desired, can be incorporated in a paste-like foodstuff such as ice cream or mayonnase, thereby providing these paste-like foodstuffs with smooth and oily texture.

The above aqueous paste-like composition containing from 5 to 40% by weight on the dry basis of the dietary fibers as hydrogel with a particle size of not greater than 80 μm can be produced, for example, as described below. That is, the hydrogel of the dietary fibers is pulverized to a particle size of not greater than 80 μm and the resultant pulverization product are subjected to acid hydrolysis as required. When acid hydrolysis is applied, the product is neutralized and the resultant salt is removed.

This is to be explained more specifically taking konjak gel as an example. Commercially available "konjak" has a solid content of not greater than about 3%, which is mechanically pulverized, if necessary, with addition of water. "Konjak" can be pulverized easily by such mechanical pulverization to about 40 μm particle size on the average. The thus prepared pulverization product is less viscous and not pasty as it is. It can be formed into an aqueous paste-like composition by properly concentrating it. If hard "konjak" of great solid content is used, the aqueous paste-like composition can be obtained without concentration.

Acid hydrolysis is applied if desired. Pulverization to fine particles as small as about 1 μm can be attained easily by acid hydrolysis. When applying the hydrolysis, the hydrolysate is naturally neutralized and the resultant salts are removed. As the acid, there may be used either a mineral acid such as sulfuric acid or hydrochloric acid or an organic acid such as acetic acid. Desired degree of hydrolysis and, accordingly, gel of desired particle size can be obtained by controlling the temperature and the time for the hydrolysis of the gel depending on the strength of the acid and thus, aimed aqueous paste-like composition can be obtained.

Preferred hydrogel of dietary fibers as the raw material for the aqueous paste-like composition is konjak gel, agar gel, pectin-Ca or -Mg gel, alginic acid-Ca or -Mg gel, carrageenan-Ca or -Mg gel, and a mixture of two or more thereof.

In the present specification, "%" and "parts" mean, respectively, "% by weight" and "parts by weight" unless otherwise specified.

EXAMPLE 6

Acetobacter aceti subsp. xylinum ATCC 10821 was static cultured in a liquid culture medium comprising 5 g/dl of sucrose, 0.5 g/dl of yeast extract, 0.3 g/dl of potassium dihydrogen phosphate, 0.5 g/dl of ammonium sulfate and 0.05 g/dl of magnesium sulfate 7 hydrate and having a pH value of 5.0, at 25° C. for one month to obtain a gel-like layer containing about 0.5% of cellulose. The layer was washed to obtain pure gel-like cellulose free of the culture medium and the bacterial cells.

The gel-like cellulose was pulverized by a commercially available mixer at 3,000 rpm for 5 min into a liquid suspension. The suspension was equally divided into four portions to which aqueous 10, 12, 15 and 20% sodium hydroxide were added and each portion was immersed for one hour, neutralized and then partially decomposed with 3N hydrochloric acid at 100° C. for one hour. After neutralizing them respectively and removing salts by dialysis overnight, they were subjected to centrifugation at 3,000 g for 20 min to obtain four kinds of paste-like precipitates.

When a portion of each of the paste-like materials was dried and the solid contents (here, cellulose) were determined, they were from about 10–12%. The dietary fibers were rod-like shape of not greater than 1 μm length under the observation of a transmission type electron microscope.

To 82 parts of each of the four types of the pastes, 16 parts of milk, 1.5 parts of table salt, 0.03 parts of butter flavor and 0.005 parts of β-carotin were admixed.

The resulting mixtures were spreaded on bread and compared with commercially available margarine. The results are shown in Table 5.

TABLE 5

| Concentration of sodium hydroxide (%) | Number of persons who could not find difference from margarine (N/20) |
|---|---|
| 10 | 13 |
| 12 | 19 |
| 15 | 18 |
| 20 | 19 |

Preferred results were obtained by the sodium hydroxide treatment at a concentration of higher than 12% before acid hydrolysis.

EXAMPLE 6a (a) After dispersing 15 g of xanthan gum previously into 1 kg of water, the dispersion was stirred together with 300 g of an Acetobacter-produced fiber paste obtained in the method of Example 6 (10% solid content), g of vinegar, 4000 g of corn oil, 200 g of table salt, 2 g of aspartame (AP) and 2753 g of water, at 10000 rpm for 5 min in a ultra-homomixer Model UM-3 manufactured by Nihon Seiki Seisakusho Co. to obtain a dressing.

The composition of the raw materials of the dressing was as shown in Table 5A.

TABLE 5A

| | |
|---|---|
| Vinegar | 2000 g |
| Corn oil | 4000 |
| Acetobacter-formed fiber paste | 300 |
| Xanthan gum | 15 |
| Table salt | 200 |
| AP | 2 |
| Water | 3483 |
| | 10000 g |

The thus obtained dressing was an emulsion type dressing of less viscous feeling with a viscosity of not higher than 2000 cps at 25° C. Further, it remained in a stable emulsified state for more than two months when stored in a refrigerator (4° C.).

The dressing showed some calorie reduction as compared with a dressing obtained by using, instead of AP, 400 g of sugar showing the same degree of sweetness.

(b) For the comparison, another dressing was prepared quite in the same procedures as those in (a) above except for replacing 30 g of Acetobacter-produced fiber paste with 300 g of water in the composition shown in Table 5A.

The composition of the raw materials was as shown in Table 5B.

TABLE 5B

| | |
|---|---|
| Vinegar | 2000 g |
| Corn oil | 4000 |
| Xanthan gum | 15 |
| Table salt | 200 |
| AP | 2 |
| Water | 3783 |
| | 10000 g |

The thus obtained emulsified dressing had less viscous feeling at a viscosity of not higher than 200 cps at 25° C., but it showed segregation after 10 days during storage in a refrigerator (4° C.). That is, in an attempt of calorie reduction by using AP, a resultant dressing shows poor emulsion stability and shows segregation if acetobacter-produced fiber paste is not used.

EXAMPLE 7

To 10 g of crystalline cellulose AVICEL FD® (manufactured by Asahi Kasei Kogyo Co.) suspended in 500 ml of 0.1M acetic acid buffer at pH 5.0, 5 g of cellulase Onotsuka was added and the reaction was carried out at 37° C. for 24 hour with stirring from time to time. Then, centrifugation (3,000 g, 20 min) and water washing were repeated to remove the soluble substances such as glucide from the reaction product thereby obtaining a paste-like product.

The paste-like product had a solid content of about 23%. The dietary fibers were rod-like shape of not greater than 3 μm length.

EXAMPLE 8

After pulverizing the endodermis and peelings of summer oranges by a 2-liter EXCEL autohomogenizer (manufactured by Nihon Seiki Co.) at 3,000 rpm for 3 min, it was boiled at 120° C., in aqueous 2% NaOH in an amount of 10 times the volume of the pulverized endodermis and peelings, to remove soluble portions. After neutralization, it was heated in aqueous 12% NaOH at 90° C. for 60 min, during which slight shrinkage was observed. After neutralization and water washing, it was placed in 3N hydrochloric acid and subjected to partial hydrolysis by heating at 95° C. for one hour. Then, centrifugation (5,000 g, 10 min) and water washing were repeated to obtain a brown paste-like material.

The solid content was about 20%. The dietary fibers were rod-like shape of not greater than 5 μm length.

EXAMPLE 9

1 part of commercially available konjak mannan ("konjak" powder) was dissolved into 100 parts of water to prepare a colloidal solution. The solution and hexane containing 2% polyglycerin fatty acid ester type surface active agent ("CR-500" manufactured by Sakamoto Yakuhin Co.) dissolved therein were mixed at a 1:1 ratio to form a W/O emulsion using a homomixer. Then, hexane was removed under a reduced pressure at 80° C. to obtain a paste-like composition.

The solid content was about 11%.

EXAMPLE 10

50 g of soybean curd refuse (okara) dried under vacuum was finely pulverized with a fine pulverizer "National Cooking Mixer Mini Cup" (manufactured by Matsushita Denki Sangyo Co.) for 30 seconds.

The fine pulverized soybean curd refuse was suspended in one liter of 2N sodium hydroxide at 100° C. for 2 hours, cooled to 10° C. and then centrifugalized (1,000 g, 10 min) by using a centrifuge (manufactured by Tomy Co.) to recover insoluble matters. It was processed by using a DYNO mill (manufactured by Willy A. Bachofen Manufacturing Engineers, Basel 5/Switzerland, KDL type glass beads: 0.10 mmφ, 4,500 rpm, 15 min). The processed liquid was treated with 2N hydrochloric acid at 100° C. for 30 min and neutralized with an aqueous sodium hydroxide. The neutralized solution was processed by using a centrifuge (2,000 g, 10 min) and the finely pulverized soybean curd refuse was collected, which was again suspended in city water, centrifugalized (2,000 g, 10 min) and then washed. The procedures were repeated several times to obtain 50 g of paste-like material.

The solid content was about 20%. The dietary fibers were rod-like shape of not greater than 5 μm length.

EXAMPLE 11

100 g of soybean husk was treated in quite the same procedures as in Example 10 to obtain 400 g of paste-like material.

The solid content was about 19%. The dietary fibers were rod-like shape of not greater than 5 μm length.

EXAMPLE 12

10 g of used tea leaves was treated in quite the same procedures as in Example 10 to obtain 30 g of paste-like material.

The solid content was about 17%. The dietary fibers were rod-like shape of not greater than 5 μm length.

EXAMPLES 13-16

100 g of each of air-dried wheat bran, barley bran, rye bran and oat bran was finely pulverized by a pulverizer "National Cooking Mixer Mini Cup" for 3 minutes.

The pulverization products were sieved through a 50 mesh (mesh/inch) sieve to remove not-pulverized portions.

They were respectively suspended in 3 liter of 1.5M sodium hydroxide, treated at 90° C. for one hour, neutralized with hydrochloric acid and then subjected to filtration under vacuum suction using Wattman 3 MM filter paper to recover insoluble residues. Each of the residues was suspended in one liter of water and then again subjected to filtration under vacuum suction in the same manner as above. After suspending each of the resultant residues in 2 liter of water, it was processed by using a DYNO mill (Willy A. Bachohen Manufacturing Engineers, Basel 5/Switzerland, KDL type glass beads: 0.10 mmφ, 4,500 rpm, 20 min). After separating glass beads by decantation from the processed solutions, the solutions were centrifugalized by using a centrifuge (manufactured by Tomy Co.) at 3,000 g for 20 min, to recover insoluble matters.

Each of the insoluble matters was processed with one liter of 2N hydrochloric acid at 95° C. for one hour and neutralized with an aqueous sodium hydroxide. Each neutralized solution was centrifugalized (10,000 g, 20 min), to obtain a very finely pulverized matter. Each of the matters was suspended again in one liter of water, subjected to centrifugation (10,000 g, 10 min) and then washed with water. The procedures were repeated several times to obtain paste-like materials in amounts of about 120 g, 105 g, 95 g and 130 g, respectively.

The solid contents in each of the paste-like materials were 15%, 19%, 16% and 16%, respectively, and all of the dietary fibers were rod-like shape of not greater than 5 μm length.

When the four types of the paste-like material were compared with margarine by the method as described in Example 6, it was found that they gave margarine-like texture.

EXAMPLE 13a (a) After dispersing 7.5 g of xanthan gum previously into 207.5 g of water, the dispersion was pre-mixed with 75 g of table salt, 1000 g of wheat bran fiber paste (solid content: 15%, grain size: 4 μm) prepared in the same way as in Example 13, 500 g of vinegar, 800 g of yolk (9.4% of lecithin content), 10 g of mustard and 5000 g of water in a vacuum emulsifying device. Then, while adding 3250 g of cotton seed oil at a rate of 200 g/min, they were stirred moderately and emulsified at about 2000 rpm and then mixed under stirring at a high speed under a reduced pressure of 60 to 65 mmHg for 2 min to obtain a flowing mayonnaise-like dressing.

The composition of the raw materials of the thus obtained dressing was as shown in Table 5C.

TABLE 5C

| Cotton seed oil | 3250 g |
|---|---|
| Vineger | 500 |
| Yolk | 800 |
| Wheat bran fiber paste | 1000 |
| Table salt | 75 |
| Xanthan gum | 7.5 |
| Mustard | 10 |
| Water | 4357.5 |
| | 10000 g |

The dressing showed a viscosity of as low as 500 cps at 25° C. and had a flowable property. Further, it remained in a stable emulsified state for one month storage in a refrigerator (4° C.).

(b) For the comparison, a dressing was prepared quite in the same procedures as those in (a) above except for replacing 1000 g of the wheat bran fiber paste with 1000 g of water in the composition shown in Table 5C.

The composition of the raw materials was as shown in Table 5D.

TABLE 5D

| Cotton seed oil | 3250 g |
|---|---|
| Vineger | 500 |
| Yolk | 800 |
| Table salt | 75 |
| Xanthan gum | 7.5 |
| Mustard | 10 |
| Water | 5357.5 |
| | 10000 g |

The thus prepared dressing had a viscosity of not higher than 500 cps at 25° C. and a flowable property, but it showed segregation after three days storage in a refrigerator (4° C.). Then, the emulsion stability was poor.

EXAMPLE 17

The paste-like materials obtained in Examples 7–12 were respectively blended with butter flavor, β-carotin, table salt and milk in the same manner as in Example 6 to obtain margarine-like products. They were compared with the margarine-like products obtained in Example 6. Comparison was also made for 1:1 mixtures of two of the various products. The results are shown in Table 6.

TABLE 6

| | | Evaluation | | |
|---|---|---|---|---|
| Raw material | Exp. No. | Margarine-like | Rough | Watery |
| Bacterial cellulose | 6 | Yes | No | No |
| AVICEL FD ® | 7 | Yes | No | No |
| Summer orange endodermis | 8 | Some | A little | No |
| Konjak mannan | 9 | Some | No | A little |
| Soybean curd refuse | 10 | Some | No | No |
| Soybean husk | 11 | Yes | No | No |
| Used tea leaves | 12 | Yes | No | No |
| Bacterial cellulose + soybean curd refuse (1:1) | 12 | Yes | No | No |
| Bacterial cellulose + konjak mannan (1:1) | | Yes | No | No |
| Soybean husk + konjak mannan (1:1) | | Yes | No | No |

EXAMPLE 17A (a) After previously dispersing 10 g of xanthan gum into 1 kg of water, the dispersion was stirred with 263 g of apple fiber paste (solid content: 19%, grain size: 4 μm), 10 g of tabasco, 300 g of garlic seasoning oil, 200 g of olive oil (not-purified oil) and 9217 g of consommé soup at 10000 rpm for 5 min by using a ultra-homomixer Model UM-3 manufactured by Nihon Seiki Seisakusho Co., to obtain a soup.

The composition of the raw materials of the thus prepared soup was as shown in Table 6A.

TABLE 6A

| | |
|---|---|
| Garlic seasoning oil | 300 g |
| Olive oil | 200 |
| Apple fiber paste | 263 |
| Xanthan gum | 10 |
| Tabasco | 10 |
| Consommé soup | 9217 |
| | 10000 g |

The resultant soup was less viscous having a visocosity of not higher than 150 cps at 25° C. (sold soup). When the soup was stored in a refrigerator (4° C.), it remained in a stable emulsified state for three weeks.

(b) For the comparison, a soup was prepared quite in the same procedures as those in (a) above except for replacing 263 g of the apple fiber paste with 263 g of consommé soup in the composition shown in Table 6A.

The composition of the raw materials was as shown in Table 6B.

TABLE 6B

| | |
|---|---|
| Garlic seasoning oil | 300 g |
| Olive oil | 200 |
| Xanthan gum | 10 |
| Tabasco | 10 |
| Consommé soup | 9480 |
| | 10000 g |

The thus prepared soup was less viscous having a viscosity of not higher than 150 cps at 25° C. But, when the soup was stored in a refrigerator (4° C.), it showed segregation after three days. That is, the emulsion stability is poor without using an apple fiber paste.

EXAMPLE 17B (a) After previously dispersing 10 g of guaiac gum into 1000 g of water, the dispersion was stirred together with 200 g of corn oil containing 50 g of lecithin dissolved therein, 10 g of chocolate flavour, 10 g of AP, 208 g of burdock fiber paste (solid content: 12%, grain size: 4 µm) and 9512 g of water and emulsified at 8000 rpm for 7 min by using a ultra-homomixer Model UM-3 manufactured by Nihon Seiki Seisakusho Co., to obtain a soft drink.

The composition of the thus prepared soft drink was as shown in Table 6C.

TABLE 6C

| | |
|---|---|
| Corn oil | 200 g |
| lecithin | 50 |
| AP | 10 |
| Chocolate flavour | 10 |
| Burdock fiber paste | 208 |
| Guaiac gum | 10 |
| Water | 9512 |
| | 10000 g |

The soft drink had a viscosity of as low as not higher than 200 cps at 25° and was delicious to drink. It remained in a stable emulsified state for two months when stored in a refrigerator (4° C.).

(b) For the comparison, another soft drink was prepared quite in the same procedures as those in (a) above except for replacing 208 g of the burdock fiber paste with 208 g of water in the material composition shown in Table 6C.

The composition of the raw materials was as shown in Table 6D.

TABLE 6D

| | |
|---|---|
| Corn oil | 200 g |
| Lecithin | 50 |
| AP | 10 |
| Chocolate flavour | 10 |
| Guaiac gum | 10 |
| Water | 9720 |
| | 10000 g |

The thus prepared soft drink had a viscosity of not higher than 200 cps at 25° C., but it showed segragation when stored in a refrigerator (4° C.) after five days. That is, soft drinks prepared without using burdock fibers are poor in the emulsion stability.

EXAMPLE 18

The paste-like material obtained in Example 6 was blended with commercially available hand cream "New Kitchen Cream" (manufactured by Kanebo Co.) as shown in Table 7 and applied onto skin.

TABLE 7

| Ratio of paste-like material in Example 6 and commercially available hand cream | Stickiness during and after use |
|---|---|
| 0:1 | sticky |
| 1:1 | None |
| 1:1 (containing 3% ethanol) | None |
| 1:0 (containing 3% glycerine) | None |

Stickiness was removed by blending the product of the present invention.

EXAMPLE 19

100 g of commercially available "konjak" was mixed with 900 ml of water by using a fruit juice mixer (3,000 rpm, 3 min.) After heating the mixture at 80°–95° C. for 30 min, it was centrifugalized at 3,000 g for 15 min to recover precipitates, which were suspended in one liter of water. Then, the suspension was added with about 0.7 ml of 0.1N hydrochloric acid to adjust the pH to 1, and then autoclaved at 120° C. for 30 min. After neutralization by using 0.1N sodium hydroxide, centrifugation was applied at 3,000 g to obtain a paste-like material.

The solid content was about 12% and the particle size of the hydrogel was not greater than 35 µm.

EXAMPLE 20

Four blocks of commercialy available "konjak" were cut into small cubes and mixed with 2 kg of water. The mixture was pulverized with a mixer (OSTERIZER) for 5 min. Then the pulverized mixture was hydrolyzed with 1 kg of concentrated hydrochloric acid at 65° C. for 2.5 hr., neutralized with sodium hydroxide and centrifugalized (13,000 g, 5 min) to recover precipitates. The precipitates were again suspended in water and subjected to centrifugation repeatedly in the same manner, to obtain 100 g of tasteless and odorless paste-like material (product of the invention).

The solid content of the paste-like material (dietary fibers) was 12%. The average particle size of the hydrogel of the paste-like material was 20 μm, measured by a laser diffraction type particle size distribution measuring device "LA-500" (manufactured by Horiba Seisakusho Co.) and showed extremely oily property.

Mayonnase prepared from, and composed of, 34 parts of the paste-like material, 40 parts of corn oil, 19 parts of yolk-spice mix and 7 parts of vinegar (also product of the present invention) showed no substantial difference from usual mayonnase in view of texture and attained 40% calorie reduction. For the purpose of comparison, another mayonnase was prepared from, and composed of, 74 parts of corn oil, 19 parts of yolk-spice mix and 7 parts of vinegar (control).

The two types of mayonnase were served to 30 consumer panelists to let them choose preferred one. As a result, 24 panelists showed preference to the mayonnase of the invention, five panelists showed preference to the control mayonnase and one panelist showed no preference.

As a result, it was found that the mayonnase made from the paste-like material according to the present invention was acceptable to consumers since it was nice in taste and reduced in calorie.

EXAMPLE 21

Four blocks of commercially available "konjak" were cut into small cubes and mixed with 1 kg of water. The mixture was pulverized with a mixer (OSTERIZER) for 5 min and then treated with a Virtis homogenizer (available from Maruto Associates) at 40,000 rpm for 10 min. The homogenized mass was subjected to centrifugation (12,000 g, 5 min). The thus obtained paste-like material had a solid content of 10% and an average particle size of the hydrogel of 40 μm and showed a smooth property.

Ice cream prepared from 32 parts of the paste-like material, 11 parts of skim milk, 11 parts of sugar, 8% of starch syrup, one part of yolk, 0.5 parts of cream, 0.3 parts of gelatine, 0.2 parts of tamarind gum, 0.1 part of locust bean gum, 0.2 parts of vanilla flavor and 35.7 parts of water showed substantially the same texture as usual high quality ice cream and showed 60% calorie reduction.

EXAMPLE 22

4 g of powdery agar was dissolved in 400 ml of water, boiled, cast into a vessel and then cooled to obtain agar gel. The gel was finely pulverized with a DYNO mill (glass beads: 0.50 mmφ and 0.25 mmφ, 1,500 rpm, each processed by 2 cycles) and subjected to centrifugation (12,000 g, 5 win) to obtain smooth paste-like material with 13% solid content and the hydrogel had an average particle size of 50 μm.

A spread prepared from 75 parts of the paste-like material, 10 part of whipped cream, 0.1 part of aspartame, 0.1 part of lemon oil and 15 parts of water was smooth and reduced in calorie.

The spread was subjected to functional evaluation by 20 expert panelists (five score full mark). The results are as shown in Table 8.

TABLE 8

| | Evaluation (score) | Number of panelists |
|---|---|---|
| Very delicious | (4) | 3 |
| Delicious | (4) | 15 |

TABLE 8-continued

| | Evaluation (score) | Number of panelists |
|---|---|---|
| Ordinary | (3) | 2 |
| Unpalatable | (2) | 0 |
| Extermely unpalatable (one score) | (1) | 0 |

The average score was 4.1, showing that the past-like material according to the present invention was preferred food material.

EXAMPLE 23

An aqueous 0.5% solution of sodium alginate (manufactured by Kokusan Kagaku Co.) was slowly added dropwise to an aqueous 2% solution of calcium chloride by using a constant flow pump. When the particles had sufficient strength by standing still for 30 min of the dropping, the spheres of the gel were washed with water, an equi-volume of water was added and then they were pulverized with a mixer (OSTERLIZER) for 2 min. An equi-volume of concentrated hydrochloric acid was added to the resulting suspension, followed by hydrolysis at 50° C. for 3 hours. Neutralization with sodium hydroxide was carried out and then centrifugation (13,000 g, 5 min) to recover precipitates. After suspending the precipitates again in water, the centrifugation was repeated in the same manner to obtain tasteless and odorless paste-like material.

The paste-like material had a solid content of 11%, the average particle size of the hydrogel was 30 μm, and it showed an oily property.

The paste-like material was subjected to a functional evaluation by 20 expert panelists. The results are as shown in Table 9 and it was evaluated to have oily texture.

TABLE 9

| Evaluation | Number of panelists |
|---|---|
| Oily | 16 |
| Viscous | 2 |
| Watery | 1 |
| Rough | 1 |

EXAMPLE 24

An aqueous 1% solution of pectin "LM-SN-325" (manufactured by Unipectin Co.) was slowly dropped into an aqueous 2% solution of calcium lactate by using a constant flow pump.

When the particles had sufficient strength by standing still for 30 min after dropping, the spheres of the gel were washed with water, an equi-volume of water was added and they were pulverized by a mixed (OSTERLIZER) for 2 min. An equi-volume of concentrated hydrochloric acid was added to the suspension, which was hydrolyzed at 50° C. for 3 hours, neutralized with sodium hydroxide and then centrifugalized (13,000 g, 5 min) to recover precipitates. After suspending the precipitates again into water, centrifugation was repeated in the same manner to obtain tasteless and odorless paste-like material.

The paste-like material had a solid content of 13% and the average particle size of the hydrogel was 35 μm.

Dressing prepared from 20 parts of the paste-like material, 5 parts of sugar, 2.5 parts of table salt, 5 parts of seasoning and spice, 13 parts of vinegar and 54.5 parts of water was organoleptically acceptable and reduced in calories.

EXAMPLE 25

One part of commercially available konjak mannan ("konjak" powder) and one part of calcium chloride were dissolved in 100 parts of water to prepare a colloidal solution. After mixing the solution with 200 parts of hexan containing a surface active agent "CR-500" dissolved therein at 20% concentration, they were stirred at 3,000 rpm for 20 min by using an EXCEL autohomogenizer for 20 min to form a W/O emulsion. While continuously stirring the liquid mixture, 3 parts of 6N sodium hydroxide was added dropwise over 5 min to the liquid mixture. It was heated to about 50° C. and then allowed to cool to room temperature for 30 min. Then, after leaving for three days, hydrochloric acid was gradually added dropwise for neutralization. The neutralized solution was desalted by repeating centrifugation and water addition. Then, the product was centrifugalized and the hexane was evaporated from the precipitated residue to obtain a paste-like composition.

When the paste-like composition was observed under optical microscope, spheres konjak gel of 0.5 to 5 μm diameter were observed. The solid content was 5.3%.

EXAMPLE 26

One part of commercially available konjak mannan ("konjak" powder) and one part of calcium chloride were dissolved in 100 parts of water to prepare a colloidal solution. After heating the solution to 90° C., one part of 6N sodium hydroxide was added dropwise by using an EXCEL autohomogenizer for 5 min under stirring at 3,000 rpm. While maintaining the temperature at about 80° C. as it was, the mass was left for 30 min. After cooling to room temperature, hydrochloric acid was added dropwise gradually for neutralization. The neutralized solution was desalted and the precipitates were recovered by repeating the centrifugation and addition of water.

The precipitates showed a paste-like touch. The hydrogel was rod-like shape of not greater than 5 μm length. The solid content was 5.6%.

EXAMPLE 27

One part of commercially available konjak mannan ("konjak" powder) was dissolved in 100 parts of water to prepare a colloidal solution. The colloidal solution was added dropwise into 200 parts of an aqueous 4% suspension of $Ca(OH)_2$ at 90° C. under vigorous stirring by using a YAMATO ultra disperser (manufactured by Yamato Kagaku Co.). After the completion of the dropping, stirring was continued for further 20 min. After cooling to room temperature, the solution was centrifugalized at 10,000 g for 40 min to obtain precipitates. The precipitates were washed with water by repeating centrifugation and suspension in water.

When the resultant precipitates were observed under an optical microscope, fibrous konjak gel of 1 μm width was recognized. The fibrous konjak gel was suspended at 0.1% solid concentration in water, which suspension was adjusted with hydrochloric acid to pH 1 and then autoclaved at 120° C. for 30 min.

After neutralization, a paste-like composition was obtained by centrifugation. The solid content was 5.5% and the hydrogel was rod-like shape of not greater than 5 μm length.

EXAMPLE 28

Four blocks of commercially available "konjak" were cut into small cubes and pulverized together with 2 kg of water in an OSTERIZER mixer for 5 min (A) and such pulverized products were further processed by a Virtis homogenizer (available from Malto Associates) for 10 min (B). 1 kg of concentrated hydrochloric acid was added to each of (A) and (B) above, to hydrolyze at 65° C. for 2.5 hours. After neutralizing with sodium hydroxide, they were respectively subjected to centrifugation (13000 G for 5 min) to collect precipitates.

After suspending the precipitates again in water, the centrifugation was repeated in the same manner to obtain paste-like materials both having a solid content of about 12%. They had an average grain size of 20 μm (A) and 4 μm (B), respectively.

Mayonnaise was prepared with a formulation comprising 34 parts by weight of each of the paste-like material, 40 parts by weight of corn oil, 19 parts by weight of yolk spice mix and 7 parts by weight of vinegar.

The thus obtained two kinds of mayonnaise were served to 15 trained panelists to let them choose preferred one. As a result, 12 panelists showed preference to the mayonnaise (A), two panelists showed preference to the mayonnaise (B) and one panelist showed no preference. The panelists showing preference to the mayonnaise (A) gave comments that the mayonnaise (A) was voluminuous and gave no pasty feeling as compared with the mayonnaise (B). Thus, it was confirmed that the grain size of the paste-like material is preferably 20 μm rather than 4 μm.

EXAMPLE 29

4 g of powdery agar was dissolved in 400 cc of water, boiled, cast into a vessel and then cooled to obtain agar gel. The gel was finely pulverized with an OSTERIZER mixer and then further processed in a Virtis homogenizer (available from Maruto Associates) for 10 min. 1 kg of concentrated hydrochloric acid was added to the pulverizates to apply hydrolysis at 65° C. for from 2.5 to 10 hours, i.e., 2.5, 5, 7.5 and 10 hours, to obtain hydrolyzates of various average grain sizes. The reaction was terminated by neutralizing with the use of sodium hydroxide. After washing with water and removing salt, the products were subjected to centrifugation (13000 G, for 5 min) to collect paste-like materials each having a solid content of about 12%.

The average grain size of each of the paste-like materials A, B, C and D was measured by a laser diffraction type particle size distribution measuring device LA-500 manufactured by Horiba Seisakusho Co., and the oily feeling was tested by the sensory evaluation by five-trained panelists. The results are shown in Table 10.

TABLE 10

|  | A | B | C | D |
|---|---|---|---|---|
| Hydrolysis time (h) | 2.5 | 5 | 7.5 | 10 |
| Average grain size (μm) | 15 | 5 | 3 | 1 |
| Sensory evaluation | ⊚ | ○ | Δ | X |

⊚ : smooth and oily
○ : smooth
Δ: watering
X: pasty

From the results shown in Table 10, it was found that the average grain seze of the paste-like material is preferably not less than 5 μm.

What is claimed is:

1. A low calorie mayonnaise product or margarine product comprising as a substitute for part or all of protein, carbohydrate, oil, fat or a mixture thereof, 0.7 to 10% by weight of paste-like konjak mannan hydrogel, based on total weight of said product and measured on the basis of dry konjak mannan, said konjak mannan hydrogel having a particle size of 5 to 80 μm and a water holding capacity of at least 9 grams of water per gram of dry konjak mannan, obtained by mechanically pulverizing konjak gel in the presence of water and hydrolyzing the resultant pulverized mixture to partially decompose it, followed by centrifugation to form a centrifuged product.

2. The low calorie mayonnaise or margarine product of claim 1 wherein the centrifuged product after the centrifugation is suspended in water and subjected to centrifugation repeatedly to obtain an odorless paste-like material.

3. The low calorie mayonnaise or margarine product of claim 1 wherein the hydrolysis is an acid hydrolysis by means of a mineral acid or an organic acid.

4. The low calorie mayonnaise or margarine product of claim 1 wherein the average particle size of said konjak mannan hydrogel is about 40 μm.

5. The low calorie mayonnaise or margarine product of claim 1 which comprises 1.0 to 2.0% by weight of konjak mannan hydrogel.

6. The low calorie mayonnaise or margarine product of claim 1 wherein the konjak mannan hydrogel has a water holding capacity of 11.5 grams of water per gram of dry konjak mannan.

7. The low calorie mayonnaise or margarine product of claim 3 wherein the acid is selected from the group consisting of sulfuric acid, hydrochloric acid and acetic acid.

* * * * *